(12) United States Patent
Blattner et al.

(10) Patent No.: US 7,989,181 B2
(45) Date of Patent: Aug. 2, 2011

(54) METHODS AND COMPOSITIONS FOR PRODUCING RECOMBINANT PROTEINS USING A GENE FOR TRNA

(75) Inventors: Frederick R. Blattner, Madison, WI (US); John Walter Campbell, Oak Park, IL (US); Guy Plunkett, Madison, WI (US)

(73) Assignee: Scarab Genomics, LLC, Madison, WI (US)

( * ) Notice: Subject to any disclaimer, the term of this patent is extended or adjusted under 35 U.S.C. 154(b) by 3 days.

(21) Appl. No.: 12/294,369

(22) PCT Filed: Apr. 23, 2007

(86) PCT No.: PCT/US2007/067232
§ 371 (c)(1),
(2), (4) Date: Sep. 24, 2008

(87) PCT Pub. No.: WO2007/124493
PCT Pub. Date: Nov. 1, 2007

(65) Prior Publication Data
US 2009/0053766 A1    Feb. 26, 2009

Related U.S. Application Data

(60) Provisional application No. 60/793,755, filed on Apr. 22, 2006.

(51) Int. Cl.
*C12P 21/04* (2006.01)
*C12N 5/10* (2006.01)
*C12N 1/20* (2006.01)
*C12N 1/19* (2006.01)

(52) U.S. Cl. .................. 435/69.1; 435/348; 435/252.3; 435/254.2

(58) Field of Classification Search .................. None
See application file for complete search history.

(56) References Cited

U.S. PATENT DOCUMENTS 6,270,988 B1 *  8/2001  Brinkmann et al. .......... 435/69.1
6,989,265 B2 *  1/2006  Blattner et al. ............ 435/252.8

FOREIGN PATENT DOCUMENTS

WO    WO 00/44926 A1    8/2000

OTHER PUBLICATIONS

Del Tito et al (Effect of minor isoleucyl tRNA on heterologous protein translation in *Escherishia coli* (Journal of Bacteriology 1995, vol. 177, p. 7086-7091).*
Novy et al (Overcoming the codon bias of *E. coli* for enhanced protein expression inNovations, No. 12, Jun. 2001.*
Gourse et al (Proc. Natl. Acad. Sci. USA vol. 82, pp. 1069-1073.*
Condon et al 1993. Depletion of functional ribosomal RNA operons in *Escherichia coli* causes increased expression of the remaining intact copies EMBO J. 12:4305-4315.*
Condon, C., C. Squires, and C. L. Squires. 1995. Control of rRNA transcription in *Escherichia coli*. Microbiol. Rev. 59:623-645.*
Brosius, J., et al., "Consruction and Fine Mapping of Recombinant Plasmids Containing the RRNB Ribosomal RNA Operon of *E. coli*," Plasmid, vol. 6, No. 1, pp. 112-118 (1981) XP009098966.
Kiesewetter, S., et al., "Sequences of Three Minor tRNAsARG from *E. coli*," Nucleic Acids Research, vol. 15, No. 7 pp. 3184 (1987) XP002477292.
Roberts, J.W., et al., "Molecular Mechanism for Missense Suppression in *E. coli*," Nature, vol. 25, No. 465, pp. 412-414(1974) XP009099376.
International Search Report of PCT/US2007/067232 dated Oct. 29, 2008.

* cited by examiner

*Primary Examiner* — Manjunath Rao
*Assistant Examiner* — Kagnew H Gebreyesus
(74) *Attorney, Agent, or Firm* — Morgan, Lewis & Bockius

(57) ABSTRACT

The invention relates to host cells with improved protein expressed properties. The host cells comprise rare tRNA genes within the one or more rRNA operons.

11 Claims, 3 Drawing Sheets

FIGURE 1

| | | codon usage cumulative frequency (per thousand) | | tRNA gene copy number [content] | | | codon usage cumulative frequency | | tRNA gene copy number | |
|---|---|---|---|---|---|---|---|---|---|---|
| | codon | E. coli | T4 | anti-codon | E. coli | T4 | M. tuberculosis | D29 | M. tuberculosis | D29 |
| Arg | CGU | 20.9 | 19.0 | ACG | 4 [0.9] | | 8.4 | 6.5 | 1 | |
| | CGC | 22.0 | 5.8 | | | | 28.4 | 20.6 | | |
| | CGA | 3.6 | 5.5 | | | | 7.2 | 9.6 | 1 | |
| | CGG | 5.4 | 1.2 | CCG | 1 [minor] | | 24.6 | 21.2 | | |
| | AGA | 2.1 | 10.2 | UCU | 2 [minor] | 1 | 1.3 | 0.9 | 1 | |
| | AGG | 1.2 | 1.9 | CCU | 1 [minor] | | 3.2 | 5.3 | 1 | |
| | | 55.2 | 43.6 | | | | 73.0 | 64.2 | | |
| Leu | UUA | 13.9 | 27.6 | UAA | 1 [0.25] | 1 | 1.6 | 0.0 | 1 | |
| | UUG | 13.7 | 10.8 | CAA | 1 [0.2] | | 17.9 | 5.6 | 1 | |
| | CUU | 11.0 | 18.3 | | | | 5.4 | 4.6 | | |
| | CUC | 11.1 | 4.1 | GAG | 1 [0.3] | | 17.3 | 26.4 | 1 | |
| | CUA | 3.9 | 6.9 | UAG | 1 [minor] | | 4.8 | 1.6 | 1 | |
| | CUG | 52.6 | 5.7 | CAG | 4 [1.0] | | 50.4 | 44.1 | 1 | |
| | | 106.2 | 73.5 | | | | 97.4 | 82.3 | | |
| Ser | UCU | 8.5 | 24.6 | | | | 2.2 | 3.4 | | |
| | UCC | 8.6 | 3.6 | GGA | 2 [0.25] | | 11.5 | 11.6 | 1 | |
| | UCA | 7.2 | 18.1 | UGA | 1 [0.25] | 1 | 3.5 | 3.0 | 1 | |
| | UCG | 8.9 | 3.7 | CGA | 1 [0.05] | | 19.3 | 17.9 | 1 | |
| | AGU | 8.8 | 10.7 | | | | 3.5 | 2.4 | | |
| | AGC | 16.1 | 5.6 | GCU | 1 [0.25] | | 14.5 | 12.1 | 1 | |
| | | 58.1 | 66.3 | | | | 54.5 | 50.4 | | |
| Ala | GCU | 15.3 | 31.2 | | | | 10.9 | 17.5 | | |
| | GCC | 25.5 | 5.3 | GGC | 2 [0.3] | | 59.9 | 36.9 | 1 | |
| | GCA | 20.1 | 19.6 | UGC | 3 [1.0] | | 12.8 | 12.1 | 1 | |
| | GCG | 33.6 | 6.3 | | | | 48.5 | 33.9 | 1 | |
| | | 94.6 | 62.4 | | | | 132.1 | 100.4 | | |
| Gly | GGU | 24.7 | 27.5 | | | | 18.9 | 15.4 | | |
| | GGC | 29.6 | 8.1 | GCC | 4 [1.1] | | 51.4 | 42.6 | 1 | |
| | GGA | 8.0 | 19.5 | UCC | 1 [0.15] | 1 | 9.9 | 8.5 | 1 | |
| | GGG | 11.1 | 3.9 | CCC | 1 [0.1] | | 19.3 | 15.8 | 1 | |
| | | 73.5 | 59.1 | | | | 99.5 | 82.3 | | |
| Pro | CCU | 7.0 | 14.4 | | | | 3.4 | 5.5 | | |
| | CCC | 5.5 | 1.2 | GGG | 1 [minor] | | 17 | 15.0 | 1 | |
| | CCA | 8.4 | 13.7 | UGG | 1 [0.3] | | 6.1 | 4.5 | 1 | |
| | CCG | 23.2 | 5.0 | CGG | 1 [0.3] | | 31.3 | 28.9 | 1 | |
| | | 44.1 | 34.2 | | | | 57.8 | 53.9 | | |
| Thr | ACU | 9.0 | 27.8 | | | | 3.7 | 4.3 | | |
| | ACC | 23.4 | 6.3 | GGU | 2 [0.8] | | 35.3 | 31.0 | 1 | |
| | ACA | 7.1 | 17.1 | UGU | 1 [0.1] | 1 | 4.5 | 3.9 | 1 | |
| | ACG | 14.4 | 5.3 | CGU | 1 [0.1] | | 15.6 | 19.3 | 1 | |
| | | 53.9 | 56.4 | | | | 59.1 | 58.5 | | |
| Val | GUU | 18.3 | 31.5 | | | | 8.0 | 6.5 | | |
| | GUC | 15.3 | 5.5 | GAC | 2 [0.4] | | 32.7 | 39.6 | 1 | |
| | GUA | 10.9 | 20.0 | UAC | 5 [1.05] | | 4.7 | 3.7 | 1 | |
| | GUG | 26.4 | 6.1 | | | | 40.0 | 23.7 | | |
| | | 70.8 | 63.2 | | | | 85.4 | 73.5 | | |
| Ile | AUU | 30.3 | 50.9 | | | | 6.4 | 2.8 | | |
| | AUC | 25.1 | 11.5 | GAU | 3 [1.0] | | 33.9 | 46.7 | 1 | |
| | AUA | 4.4 | 12.2 | CAU | 2 [0.05] | 1 | 2.2 | 0.6 | | |
| | | 59.9 | 74.6 | | | | 42.5 | 50.1 | | |

FIGURE 1

| | | codon usage cumulative frequency (per thousand) | | tRNA gene copy number [content] | | | codon usage cumulative frequency | | tRNA gene copy number | |
|---|---|---|---|---|---|---|---|---|---|---|
| | codon | E. coli | T4 | anti-codon | E. coli | T4 | M. tuberculosis | D29 | M. tuberculosis | D29 |
| Asn | AAU | 17.7 | 42.8 | | | | 5.3 | 1.9 | | |
| | AAC | 21.7 | 15.0 | GUU | 4 [0.6] | | 20.0 | 30.6 | 1 | 1 |
| | | *39.4* | *57.8* | | | | *25.3* | *32.5* | | |
| Asp | GAU | 32.1 | 47.2 | | | | 15.7 | 10.7 | | |
| | GAC | 19.1 | 14.4 | GUC | 3 [0.8] | | 42.1 | 53.4 | 1 | |
| | | *51.2* | *61.6* | | | | *57.8* | *64.1* | | |
| Cys | UGU | 5.2 | 7.3 | | | | 2.2 | 1.3 | | |
| | UGC | 6.5 | 3.7 | GCA | 1 [minor] | | 6.6 | 7.4 | 1 | |
| | | *11.7* | *11.0* | | | | *8.8* | *8.7* | | |
| Gln | CAA | 15.3 | 21.7 | UUG | 2 [0.3] | 1 | 8.1 | 3.8 | 1 | |
| | CAG | 28.8 | 11.1 | CUG | 2 [0.4] | | 22.7 | 31.4 | 1 | 1 |
| | | *44.2* | *32.8* | | | | *30.8* | *35.2* | | |
| Glu | GAA | 39.4 | 60.0 | UUC | 4 [0.9] | | 16.1 | 14.7 | 1 | |
| | GAG | 17.8 | 10.8 | | | | 30.5 | 51.8 | 1 | 1 |
| | | *57.3* | *70.8* | | | | *46.6* | *66.5* | | |
| His | CAU | 12.9 | 13.5 | | | | 6.4 | 2.6 | | |
| | CAC | 9.7 | 3.7 | GUG | 1 [0.4] | | 15.8 | 19 | 1 | |
| | | *22.7* | *17.3* | | | | *22.0* | *21.6* | | |
| Lys | AAA | 33.6 | 64.1 | UUU | 6 [1.0] | | 5.3 | 3.4 | 1 | |
| | AAG | 10.3 | 17.5 | | | | 15.0 | 41.9 | 1 | |
| | | *43.9* | *81.6* | | | | *20.3* | *45.3* | | |
| Phe | UUU | 22.3 | 33.3 | GAA | 2 [0.35] | | 6.2 | 1.2 | | |
| | UUC | 16.6 | 11.1 | | | | 23.3 | 33.9 | 1 | |
| | | *38.9* | *44.4* | | | | *29.5* | *35.1* | | |
| Tyr | UAU | 16.2 | 33.8 | | | | 6.1 | 1.5 | | |
| | UAC | 12.2 | 9.7 | GUA | 3 [0.5] | | 14.7 | 27.5 | 1 | 1 |
| | | *28.4* | *43.5* | | | | *20.8* | *29.0* | | |
| Met | AUG | 27.9 | 26.7 | CAU | 5 [0.8] | | 18.4 | 21.2 | 3 | |
| Trp | UGG | 15.2 | 14.1 | CCA | 1 [0.3] | | 14.7 | 20.3 | 1 | 1 |

The total number of codons is 1363498 (4290 protein-coding genes) for *E. coli*, 53183 (271 genes) for T4, 1335687 (3924 genes) for *M. tuberculosis*, and 14789 (77 genes) for D29. Sums over synonymous codons are shown in italic. Optimal codons of *E coli* are underlined.

US 7,989,181 B2

METHODS AND COMPOSITIONS FOR PRODUCING RECOMBINANT PROTEINS USING A GENE FOR TRNA

CROSS-REFERENCE TO RELATED APPLICATIONS

This application is the National Stage of International Application Number PCT/US2007/067232, filed Apr. 23, 2007, which application claims the benefit of U.S. Provisional Application No. 60/793,755, filed Apr. 22, 2006, the contents of which are incorporated herein by reference.

FIELD OF THE INVENTION

This invention relates to modified host cells for expressing proteins and methods relating thereto by improved expression of tRNAs.

BACKGROUND OF THE INVENTION

One of the advances in modern biotechnology is the large-scale production of proteins or protein-containing gene products of interest. Bacterial host cells are often used for the production of proteins of interest because of their ability to be easily fermented in large volumes. One crucial disadvantage of numerous bacterial systems is their use of rare codons, which can be very different from the codon preference of a gene being expressed. Rare codons in bacteria are typically associated with low level expression of tRNAs bearing the complimentary anticodon. As a result, the presence of rare codons in the gene being expressed can lead to significantly reduced expression of the desired product in the bacterial host cell due to a depletion of pools of rare tRNAs.

In order to increase expression in bacterial systems, one approach has been to change rare codons in the gene being expressed to a codon occurring more frequently in the host cell that codes for the same amino acid. See U.S. Pat. No. 6,821,755. Other examples of modification of a gene of interest to replace rare codons with more favored codons may be found in Prapunwattana, et al., Mol Biochem. Parasitol. 83:93-106 (1996) and Pan, et al., Nucleic Acids Res. 27:1094-1103 (1999). This approach is limited, however, by the need to perform perhaps multiple steps of mutagenesis on the gene of interest. In addition, the process only leads to increased expression of one gene. The entire process of replacing rare codons for abundant codons must be repeated on every gene of interest.

Another approach to increase expression in bacterial systems has been to introduce into the host cells a plasmid that contains genes coding for cognate tRNAs of the rare codons. For example, several plasmids have been constructed to increase the expression of rare tRNAs. U.S. Pat. No. 6,270,988 describes plasmids containing genes for rare tRNA molecules for AGG and AGA codons for arginine. Baca, et al. Int'l. J. Parasit. 30:113, 118 (2000) describe a plasmid derived from pACYC 184 encoding tRNAs for arginine, isoleucine, and glycine: argU (AG(A/G)), ileX (AUA), and glyT (GG(A/G)). Commercially cells are also available that contain plasmids providing additional copies of rare tRNAs. Using plasmids for expressing rare tRNAs is limited by the need for a selectable marker, which increases production costs. Furthermore, the typically used high copy number plasmids can lead to genetic instability in the host cell. The art continues to need, therefore, an efficient system for producing proteins with rare codons. The present invention satisfies this need and others.

SUMMARY OF THE INVENTION

The present invention is related to a host cell with one or more rRNA operons that comprise one or more polynucleotides encoding a tRNA. The polynucleotide encoding the tRNA may be derived from a human, yeast, or from the genome of the host cell.

The polynucleotide encoding the tRNA may comprise any sequence of SEQ ID NOS: 1-7. The polynucleotide encoding the tRNA may comprise SEQ ID NOS: 1 and 7. The polynucleotide encoding the tRNA may comprise SEQ ID NOS: 1, 5 and 6. The polynucleotide encoding the tRNA may comprise SEQ ID NOS: 1, 5, 6 and 7. The polynucleotide encoding the tRNA may comprise SEQ ID NOS: 1-7.

The host cell may be a bacteria, yeast or insect cell. The host cell may also be an *E. coli*. The rRNA operon of the host cell comprising the polynucleotide encoding the tRNA may be one or more of rrnA, rrnB, rrnC, rrnD, rrnE, rrnG and rrnH. The polynucleotide encoding the tRNA may be '3 of 5S rRNA elements and 5' of terminator elements. The host cell may also comprise a gene encoding a heterologous protein. The heterologous gene may comprise one or more codons with rare tRNAs in the precursor of the host cell.

The present invention is also related to a method of producing a recombinant heterologous protein cell. A gene encoding the heterologous protein is expressed in the host cell described herein.

BRIEF DESCRIPTION OF THE DRAWINGS

FIG. 1 shows the codon frequency of *E. coli* and *M. tuberculosis*, as well as the tRNA frequency of *E. coli*.

DETAILED DESCRIPTION

Figure 2:
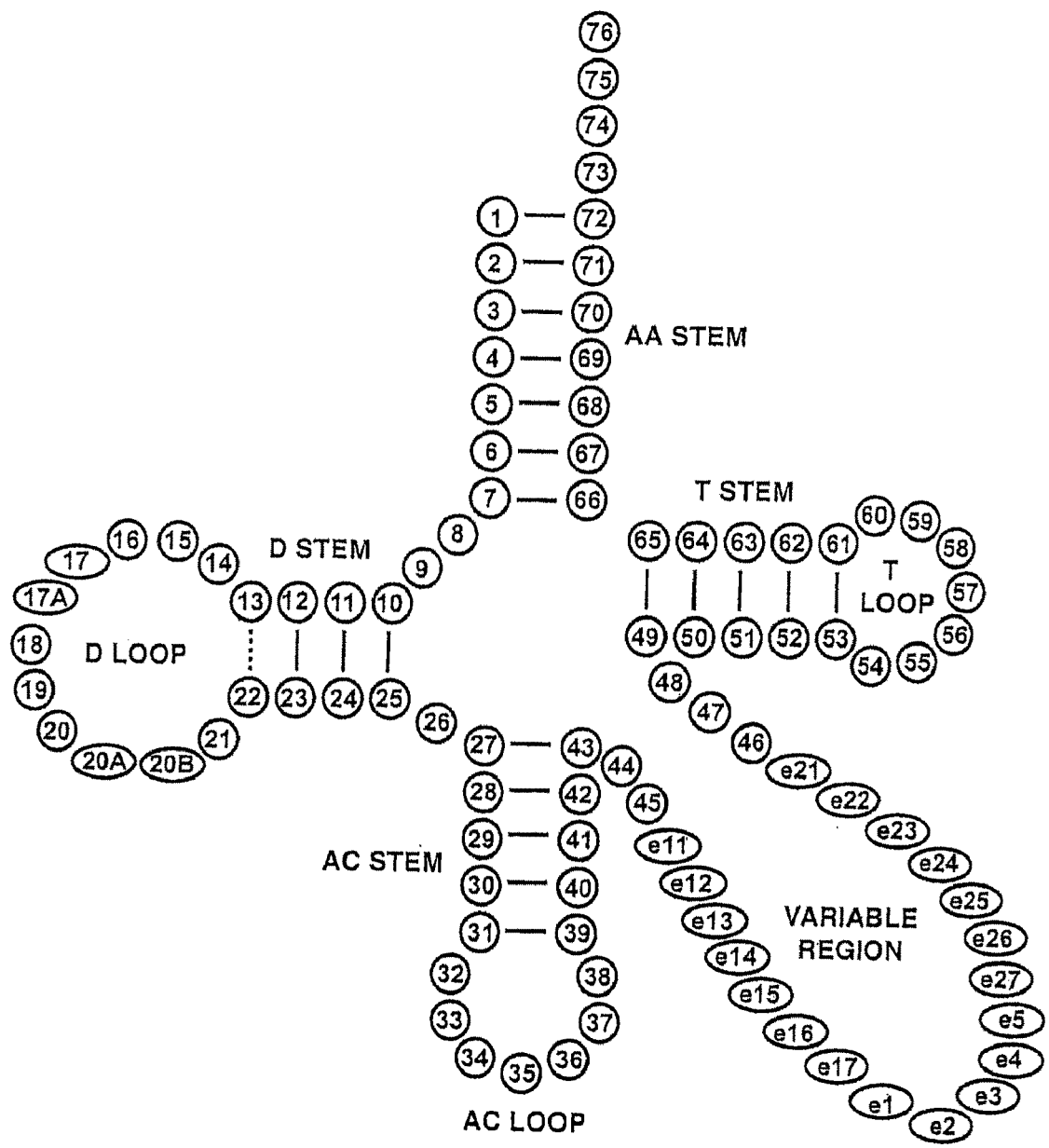
FIG. 2 depicts a tRNA cloverleaf secondary structure with the base positions labeled in the standard numbering system. The bases represented by ovals are variable in that they may or may not be present.

The present invention provides methods and compositions for increased expression of proteins in a host cell, characterized by a host cell comprising a tRNA gene in the rRNA operon of the host cell. The rRNA operon is a desirable destination for the introduction of a tRNA gene, because rRNA operons have strong promoters. This is evidenced by rRNA being the major component of cellular RNA. Furthermore, polynucleotides may be added to an rRNA operon without interfering with expression and processing of rRNAs.

Using the methods and compositions according to the invention, it is possible to achieve increased expression of proteins with increased efficiency compared with processes known from the prior art. These methods and compositions of the present invention may be useful for large-scale production of pharmaceutical products, as well as proteins for biophysical studies such as X-ray crystallography and NMR. Other possible uses will be apparent to the skilled reader.

Before the present compounds, products and compositions and methods are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

1. tRNA Genes

The present invention is related to the introduction of one or more tRNA genes into the chromosome of a host cell. Each tRNA gene may be introduced into one or more locations of one or more rRNA operons of the host cell.

The tRNA gene introduced into the rRNA operon of the host cell may be chosen based on the frequency of the codons present in the gene encoding the protein of interest compared with the frequency of codons or the frequency of cognate tRNAs expressed in the host cell. A rare tRNA gene encoding a rare tRNA or encoding a cognate tRNA of a rare codon may be introduced into an rRNA operon of the host cell. Where a gene for a protein of interest comprises multiple rare codons, genes for one or more of such cognate tRNAs may be inserted into the rRNA operon of the host cell. All tRNAs or any portion thereof, without regard to their prevalence, may also introduced into the rRNA operon, which may increase tRNA levels for all tRNAs.

A rare codon may be any codon in the host cell that is present in the host cell at a frequency less than 20, 19, 18, 17, 16, 15, 14, 13, 12, 11, 10, 9, 8, 7, 6, 5, 4, 3, 2 or 1 per thousand. A rare tRNA may be any tRNA with cell amounts, relative to Leu-tRNA, less than 0.8, 0.7, 0.6, 0.5, 0.4, 0.3, 0.1, 0.09. 0.08. 0.07, 0.06, 0.05, 0.04, 0.03, 0.02 or 0.01. FIG. 1 lists the codon frequency of *E. coli* and *M. tuberculosis*, as well as the tRNA frequency of *E. coli*.

The rare tRNA gene may be derived from the tRNA gene of the host cell. The native rare tRNA may be cloned or synthesized and inserted into the rRNA operon of the host cell using methods known in the art. The rare tRNA gene may also be derived from another organism, such as the source of the gene encoding the protein of interest. The rare tRNA may also be a synthetic, mutated, modified, suppressor, viral or bacteriophage tRNA.

The rare tRNA may be modified in the non-constant portions of the tRNA. The "constant" portions of the gene encoding a tRNA may be as follows: 8(T), 11(Y), 14(A), 15(R), 18(G), 19(G), 21(A), 24(R), 26(R), 32(Y), 33(T), 37(R), 48(Y), 52(R), 53(G), 54(T), 55(T), 56(C), 57(R), 58(A), 60(Y), 61(C), 62(Y), 74(C), 75(C) and 76(A), where Y=C or T, and R=G or A. The non-constant portions may be modified by substitutions or deletions. FIG. 2 depicts the secondary structure of a tRNA with those positions that may be deleted indicated by ovals (17, 17A, 20A and 20B in the D Loop and the bases between 45 and 46 in the Variable Region). The rare tRNA may also be a tRNA for introducing an unnatural amino acid, as described in U.S. Patent Publication No. 20040265952.

Representative examples of tRNA genes that may be used include the *E. coli* genes listed in Table 1.

TABLE 1

| Gene | Codons Recognized | Anticodon | SEQ ID NO |
|------|-------------------|-----------|-----------|
| argU | AGA, AGG | UCU | 1 |
| argW | AGG | CCU | 2 |
| argX | CGG | CCG | 3 |
| glyT | GGA, GGG | UCC | 4 |
| ilex | AUA | CAU | 5 |
| leuW | CUA, CUG | UAG | 6 |
| proL | CCC, CCU | GGG | 7 |

2. rRNA Operon

Each rRNA operon is a polycistronic suite of genes. An rRNA operon may comprise combinations of DNA encoding ribosomal RNAs (16S rRNA, 23S rRNA, and 5S rRNA), spacer tRNAs, distal tRNAs, and regulatory elements. A schematic illustration of the seven polycistronic rRNA operons of *E. coli* is presented in Table 2.

TABLE 2

| | | SEQ ID NO |
|---|---|---|
| rrnA | $P_1$-$P_2$-rrsA-ileT-alaT-rrlA-rrfA-$T_1$-$T_2$ | 8 |
| rrnB | $P_1$-$P_2$-rrsB-gltT-rrlB-rrfB-$T_1$-$T_2$ | 9 |
| rrnC | $P_1$-$P_2$-rrsC-gltU-rrlC-rrfC-aspT-trpT-T | 10 |
| rrnD | $P_1$-$P_2$-rrsD-ileU-alaU-rrlD-rrfD-thrV-rrfF-T | 11 |
| rrnE | $P_1$-$P_2$-rrsE-gltV-rrlE-rrfE-T | 12 |
| rrnG | $P_1$-$P_2$-rrsG-gltW-rrlG-rrfG-T | 13 |
| rrnH | $P_1$-$P_2$-rrsH-ileV-alaV-rrlH-rrfH-aspU-T | 14 |

KEY: regulatory elements: promoters ($P_1$, $P_2$), terminator(s) ($T_1$, $T_2$)
ribosomal rRNAs: 16S rRNA (rrs), 23S rRNA (rrl), 5S rRNA (rrf)
spacer tRNAs: tRNA$^{Ile}_1$ (ile), tRNA$^{Ala}_{1B}$ (ala), tRNA$^{Glu}_2$ (glt)
distal tRNAs: tRNA$^{Asp}_1$ (asp), tRNA$^{Thr}_1$ (thr), tRNA$^{Trp}$ (trp)

The one or more rare tRNA genes may be introduced individually or together anywhere in the operon that allows for their expression. The rare tRNA genes may be introduced into the rRNA operon 3' of $P_1$ or $P_2$. The rare tRNA genes may be introduced between the components of the rRNA operon (intergenic) or within a components of the rRNA operon (intragenic).

In determining the operon and the position on the operon at which to insert the rare tRNA genes, one of skill in the art may consider the likelihood of homologous recombination events. The site of introduction of a tRNA may result in homologous recombination between rRNA operons, due to the high degree of similarity between rRNA operons. Some experiments have shown that gene conversion events involved in the homogenization of rrn operon sequences may lead to the loss of additions made in the spacer region (Harvey and Hill 1990; Hashimoto, et al. 2003).

If it is desired to minimize homologous recombination in *E. coli*, for example, the rare tRNAs may be inserted in the 5S distal regions of the rRNA operon. The rrn operons of *E. coli* show considerable variation in their 5S distal regions, located at the 3' end of each operon. A genetic marker has been successfully introduced as a replacement for rrfH without negative effect on expression on the rrnH operon. (Ammons, et al. 1998). The rrnA, rrnB, rrnE, and rrnG operons are also candidates for the addition of rare tRNA genes since they do not already include distal tRNAs.

3. Host Cells

The present invention is also related to a host cell comprising one or more rare tRNA genes in one or more rRNA operons of the host cell. The amount of rare tRNA present in the host cell is increased compared to the levels of rare tRNA in the parent cell. The amount of rare tRNA in the host cell may be increased by greater than 1.5-, 2.0-, 2.5-, 3.0-, 3.5-, 4.0-, 4.5- or 5.0-fold.

The host cell may be derived from any parent cell which is suitable for expression of the protein of interest. The parent cell may be either eukaryotic or prokaryotic, which may be Gram-positive or Gram-negative. Representative examples of parent cells include, but are not limited to, yeast, *E. coli, B. subtilis, Streptomyces, Proteus mirabilis, Staphylococcus*, such as e.g. *S. carnosus*, and other cells available from public collections. The parent cell may be a bacteria, which may be a reduced genome bacterium as described in U.S. patent application Ser. No. 10/057,582 and in Blattner, (2004), which are both incorporated by reference herein.

4. Method of Making Host Cell

The present invention is also related to a method of making a host cell. A host cell may be made by introducing one or more rare tRNA genes into one or more rRNA operons of the parent cell. A tRNA gene may be introduced into an rRNA operon by methods well known in the art, such as may be found in Sambrook et al., "*Molecular Cloning Manual*," Cold Spring Harbor Laboratory (2001).

5. Expressible Host Cell

The present invention is also related to an expressible host cell comprising a host cell of the present invention which comprises a heterologous gene encoding a protein of interest. The heterologous gene may be operatively linked to a promoter element.

The heterologous gene may be located within the chromosome of the expressible host cell. The heterologous gene may be inserted into the chromosome of the expressible host cell using methods well known in the art, such as those methods described in Sambrook et al. (2001). The heterologous gene may also be located on a vector, with the expressible host cell comprising the vector. The vector may be capable of autonomous replication or it may integrate into the DNA of the microorganism. The vector may be any polynucleotide that is capable of transporting the heterologous gene including, but not limited to, a plasmid, cosmid, phage, phagemid, YAC or viral vector. The vector may be in a form suitable for expression of the heterologous gene in the expressible host cell. The expression vectors may be designed for expression of the protein of interest in the host cell.

The protein of interest may be any protein known in the art, such as, for example, insulin, hGH, tPA, cytokines, such as e.g. interleukins (IL) such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, interferon (IFN) alpha, IFN beta, IFN gamma, IFN omega or IFN tau, tumour necrosis factor (TNF), TNF alpha and TNF beta, TRAIL, G-CSF, GM-CSF, M-CSF, MCP-1, VEGF and antibodies.

6. Protein Expression

The present invention is also related to a method of producing a protein of interest comprising isolating the protein of interest from an expressible host cell comprising a polynucleotide encoding the protein of interest. Methods for optimizing protein expression are discussed in Hannig et al., Trends Biotechnol., 16(2):54-60 (1998), the contents of which are hereby incorporated by reference in their entirety.

The expressible host cell may constitutively express the polynucleotide encoding the protein of interest. Expression of the polynucleotide may also be regulated by one or more operatively linked regulatory sequences including, but not limited to, promoters, enhancers and other expression control elements (e.g., polyadenylation signals). Inducible regulatory sequences may be activated or repressed based on the local environment of the expressible host cell.

7. Kits

The present invention is also related to a kit comprising a container comprising host cells of the present invention. The host cells may be competent cells. The kit may optionally comprise one or more plasmids, one or more reagents for use in transformation, or instructions for use of the host cells in producing expressible host cells or proteins of interest.

The present invention is also related to a kit comprising a container comprising expressible host cells of the present invention. The expressible host cells may comprise a polynucleotide encoding a protein of interest. The kit may optionally instructions for propagating the cells or using the cells for producing the protein of interest.

The present invention has multiple aspects, illustrated by the following non-limiting example.

EXAMPLE 1

Expression of *P. falciparum* dihydropteroate synthetase (DHPS) in tRNA-Augmented *E. coli*

*E. coli* host cells of strain MDS42 are transformed by inserting argU and ileX genes into the chromosome at the 3' end of the rrnG operon. The resulting tRNA-augmented host cells are also transformed with an expression vector comprising *P. falciparum* dihydropteroate synthetase (DHPS), located downstream of a promoter, along with an antibiotic resistance marker for ampicillin. A second sample of unmodified MDS42 *E. coli* cells are transformed with the same expression vector as a control.

Overnight cultures are prepared by picking single colonies of transformed tRNA-augmented host cells and inoculating 3 ml Luria-Bertani (LB) media supplemented with ampicillin (100 µg/ml). The following morning, 100 µl of the overnight culture are used to inoculate flasks containing 2 ml of LB supplemented with ampicillin (100 µg/ml). These cultures are incubated for 3-4 hours at 37° C. until cell density $OD_{600}$ reaches 0.5-0.7. The cultures are induced by the addition of IPTG to a final concentration of 0.5 mM and then harvested 3 hours after induction. Expression of protein is monitored by SDS-PAGE of pre-induction and harvest whole cell lysates of cells with and without tRNA augmentation. Western analysis is performed on *P. falciparum* DHPS to confirm protein identity.

Enzyme assays on the tRNA-augmented cells compared with the non-augmented control cells indicate that expression of *P. falciparum* DHPS is greatly enhanced in the tRNA augmented cells.

---

What is claimed is:

1. An *E. coli* host cell comprising rRNA operons rrnA, rrnB, rrnC, rrnD, rrnE, rrnG and rrnH, wherein one or more rRNA operons of the host cell comprise one or more polynucleotides encoding a tRNA, said one or more polynucleotides comprising a sequence selected from the group consisting of SEQ ID NOS: 1-7, and wherein expression and processing of rRNA from operons rrnA, rrnB, rrnC, rrnD, rrnE, rrnG and rrnH is maintained.

2. The host cell of claim 1, wherein the rRNA operon comprises SEQ ID NOS: 1 and 7.

3. The host cell of claim 1, wherein the rRNA operon comprises SEQ ID NOS: 1, 5 and 6.

4. The host cell of claim 1, wherein the rRNA operon comprises SEQ ID NOS: 1, 5, 6 and 7.

5. The host cell of claim 1, wherein the rRNA operon comprises SEQ ID NOS: 1-7.

6. The host cell of claim 1, wherein the rRNA operon for inserting the tRNA encoding polynucleotide is selected from the group consisting of rrnA, rrnB, rrnC, rrnD, rrnE, rrnG and rrnH.

7. The host cell of claim 6, wherein the polynucleotide is inserted 3' of 5S rRNA elements and 5' of terminator elements.

8. The host cell of claim 1, wherein the host cell further comprises a gene encoding a heterologous protein.

9. A method of preparing a recombinant heterologous protein cell comprising:
   (a) providing the host cell of claim 8; and
   (b) expressing the gene encoding the heterologous protein.

10. The host cell of claim 1, wherein the host cell has a genome that is smaller than 4.00 Mb.

11. The host cell of claim 10, wherein said host cell is reduced genome strain MDS42.

* * * * *

SEQUENCE LISTING

<160> NUMBER OF SEQ ID NOS: 14

<210> SEQ ID NO 1
<211> LENGTH: 77
<212> TYPE: DNA
<213> ORGANISM: E. coli

<400> SEQUENCE: 1
gcgcccttag ctcagttgga tagagcaacg accttctaag tcgtgggccg caggttcgaa      60
tcctgcaggg cgcgcca                                                     77

<210> SEQ ID NO 2
<211> LENGTH: 75
<212> TYPE: DNA

<213> ORGANISM: E. coli

<400> SEQUENCE: 2
gtcctcttag ttaaatggat ataacgagcc cctcctaagg gctaattgca ggttcgattc    60
ctgcagggga cacca                                                    75

<210> SEQ ID NO 3
<211> LENGTH: 77
<212> TYPE: DNA
<213> ORGANISM: E. coli

<400> SEQUENCE: 3
gcgcccgtag ctcagctgga tagagcgctg ccctccggag gcagaggtct caggttcgaa    60
tcctgtcggg cgcgcca                                                  77

<210> SEQ ID NO 4
<211> LENGTH: 75
<212> TYPE: DNA
<213> ORGANISM: E. coli

<400> SEQUENCE: 4
gcgggcatcg tataatggct attacctcag ccttccaagc tgatgatgcg ggttcgattc    60
ccgctgcccg ctcca                                                    75

<210> SEQ ID NO 5
<211> LENGTH: 73
<212> TYPE: DNA
<213> ORGANISM: E. Coli

<400> SEQUENCE: 5
ggccccttag ctcagtggtt agagcaggcg actcataatc gcttggtcgc tggttcaagt    60
ccagcagggg cca                                                      73

<210> SEQ ID NO 6
<211> LENGTH: 85
<212> TYPE: DNA
<213> ORGANISM: E. coli

<400> SEQUENCE: 6
gcgggagtgg cgaaattggt agacgcacca gatttaggtt ctggcgccgc aaggtgtgcg    60
agttcaagtc tcgcctcccg cacca                                         85

<210> SEQ ID NO 7
<211> LENGTH: 83
<212> TYPE: DNA
<213> ORGANISM: E. coli

<400> SEQUENCE: 7
cggcacgtag cgcagcctgg tagcgcaccg tcatggggtg tcggggtcg gaggttcaaa    60 tcctctcgtg ccgaccaaaa atc                                           83

<210> SEQ ID NO 8
<211> LENGTH: 355
<212> TYPE: DNA
<213> ORGANISM: E. Coli

<400> SEQUENCE: 8
tgcctggcgg cagtagcgcg gtggtcccac ctgaccccat gccgaactca gaagtgaaac    60
gccgtagcgc cgatggtagt gtggggtctc ctcatgcgag agtagggaac tgccaggcat   120

| | |
|---|---|
| caaataaaac gaaaggctca gtcggaagac tgggcctttc gttttatctg ttgtttgtcg | 180 |
| gtgaacgctc tcctgagtag gacaaatccg ccgggagcgg atttgaacgt tgcgaagcaa | 240 |
| cggcccggag ggtggcgggc aggacgcccg ccataaactg ccaggcatca aattaagcag | 300 |
| aaggccatcc tgacggatgg ccttttttgca ttggcgcaga aaaaaatgcc ggatg | 355 |

<210> SEQ ID NO 9
<211> LENGTH: 355
<212> TYPE: DNA
<213> ORGANISM: E. Coli

<400> SEQUENCE: 9

| | |
|---|---|
| tgcctggcgg cagtagcgcg gtggtcccac ctgaccccat gccgaactca gaagtgaaac | 60 |
| gccgtagcgc cgatggtagt gtggggtctc cccatgcgag agtagggaac tgccaggcat | 120 |
| caaataaaac gaaaggctca gtcgaaagac tgggcctttc gttttatctg ttgtttgtcg | 180 |
| gtgaacgctc tcctgagtag gacaaatccg ccgggagcgg atttgaacgt tgcgaagcaa | 240 |
| cggcccggag ggtggcgggc aggacgcccg ccataaactg ccaggcatca aattaagcag | 300 |
| aaggccatcc tgacggatgg ccttttttgcg tttctacaaa ctcttcctgt cgtca | 355 |

<210> SEQ ID NO 10
<211> LENGTH: 368
<212> TYPE: DNA
<213> ORGANISM: E. coli

<400> SEQUENCE: 10

| | |
|---|---|
| tgcctggcgg ccgtagcgcg gtggtcccac ctgaccccat gccgaactca gaagtgaaac | 60 |
| gccgtagcgc cgatggtagt gtggggtctc cccatgcgag agtagggaac tgccaggcat | 120 |
| caaattaagc agtaagccgg tcataaaacc ggtggttgta aaagaattcg gtggagcggt | 180 |
| agttcagtcg gttagaatac ctgcctgtca cgcaggggggt cgcggggttcg agtcccgtcc | 240 |
| gttccgccac cctaattagg ggcgtagttc aattggtaga gcaccggtct ccaaaaccgg | 300 |
| gtgttgggag ttcgagtctc tccgcccctg ccagaaatca tccttagcga agctaagga | 360 |
| ttttttttt | 368 |

<210> SEQ ID NO 11
<211> LENGTH: 539
<212> TYPE: DNA
<213> ORGANISM: E. coli

<400> SEQUENCE: 11

| | |
|---|---|
| tgcctggcgg ccgtagcgcg gtggtcccac ctgaccccat gccgaactca gaagtgaaac | 60 |
| gccgtagcgc cgatggtagt gtggggtctc cccatgcgag agtagggaac tgccaggcat | 120 |
| caaatttagc gtgctgatat ggctcagttg gtagagcgca cccttggtaa gggtgaggtc | 180 |
| cccagttcga ctctgggtat cagcaccact ttttaggtta aagttcggca gattagaaaa | 240 |
| gaatttgtct ggcggcagta gcgcggtggt cccacctgac cccatgccga actcagaagt | 300 |
| gaaacgccgt agcgccgatg gtagtgtggg gtctccccat gcgagagtag ggaactgcca | 360 |
| gacatcaaat aaaacaaaag gctcagtcgg aagactgggc cttttgtttt atctgttgtt | 420 |
| tgtcggtgaa cactctcccg agtaggacaa atccgccggg agcggatttg aacgttgcga | 480 |
| agcaacggcc cggagggtgg cggcaggac gcccgccata aactgccaga catcaaatc | 539 |

<210> SEQ ID NO 12
<211> LENGTH: 197
<212> TYPE: DNA

<213> ORGANISM: E. coli

<400> SEQUENCE: 12

```
tgcctggcgg cagtagcgcg gtggtcccac ctgaccccat gccgaactca gaagtgaaac      60
gccgtagcgc cgatggtagt gtggggtctc cccatgcgag agtagggaac tgccaggcat     120
caaattagaa aaacccggt ccataaggcc ggggttttt gcatatcaat tatttgcatg      180
atgaagggaa tctcatg                                                   197
```

<210> SEQ ID NO 13
<211> LENGTH: 231
<212> TYPE: DNA
<213> ORGANISM: E. coli

<400> SEQUENCE: 13

```
tgcctggcgg ccgtagcgcg gtggtcccac ctgaccccat gccgaactca gaagtgaaac      60
gccgtagcgc cgatggtagt gtggggtctc cccatgcgag agtagggaac tgccaggcat     120
caaattatgc gaaaggccat cctgacggat ggcctttttg cattggcgca gaaaaaaatg     180
cctgatgcga cgctgcgcgt cttatactcc cacatatgcc agattcagca a              231
```

<210> SEQ ID NO 14
<211> LENGTH: 289
<212> TYPE: DNA
<213> ORGANISM: E. coli

<400> SEQUENCE: 14

```
tgcctggcgg ccgtagcgcg gtggtcccac ctgaccccat gccgaactca gaagtgaaac      60
gccgtagcgc cgatggtagt gtggggtctc cccatgcgag agtagggaac tgccaggcat     120
caaattaagc agtaagccgg tcataaaacc ggtggttgta aaagaattcg gtggagcggt     180
agttcagtcg gttagaatac ctgcctgtca cgcagggggt cgcgggttcg agtcccgtcc     240
gttccgccac ttattaagaa gcctcgagtt aacgctcgag gttttttt                  289
```